US009683941B2

(12) United States Patent
Ollikainen et al.

(10) Patent No.: US 9,683,941 B2
(45) Date of Patent: Jun. 20, 2017

(54) METHOD AND APPARATUS FOR ONLINE ANALYSIS BY LASER-INDUCED SPECTROSCOPY

(71) Applicant: OUTOTEC (FINLAND) OY, Espoo (FI)

(72) Inventors: Arto Ollikainen, Masala (FI); Kari Saloheimo, Espoo (FI); Christian Von Alfthan, Espoo (FI)

(73) Assignee: OUTOTEC (FINLAND) OY, Espoo (FI)

( * ) Notice: Subject to any disclaimer, the term of this patent is extended or adjusted under 35 U.S.C. 154(b) by 0 days.

(21) Appl. No.: 15/100,422

(22) PCT Filed: Dec. 2, 2013

(86) PCT No.: PCT/FI2013/051124
§ 371 (c)(1),
(2) Date: May 31, 2016

(87) PCT Pub. No.: WO2015/082752
PCT Pub. Date: Jun. 11, 2015

(65) Prior Publication Data
US 2016/0305887 A1    Oct. 20, 2016

(51) Int. Cl.
*G01J 3/30*    (2006.01)
*G01N 21/71*   (2006.01)
(Continued)

(52) U.S. Cl.
CPC ............. *G01N 21/718* (2013.01); *G01N 1/20* (2013.01); *G01N 1/2035* (2013.01); *G01N 21/85* (2013.01);
(Continued)

(58) Field of Classification Search
CPC .......... G01N 21/71; G01N 21/85; G01N 1/20; G01N 21/78; G01N 21/64; G01N 15/0255; G01J 3/02; G01J 3/44
See application file for complete search history.

(56) References Cited

U.S. PATENT DOCUMENTS 6,192,750 B1    2/2001  Greer et al.
2004/0011975 A1  1/2004  Nicoli et al.
(Continued)

FOREIGN PATENT DOCUMENTS

WO    WO 97/45203       12/1997
WO    WO-97/45203 A1    12/1997

OTHER PUBLICATIONS

International Preliminary Report on Patentability (Chapter II of the Patent Cooperation Treaty issued by the EPO acting as the IPEA in relation to International Application No. PCT/FI2013/051124 dated Apr. 1, 2016 (9 pages).
(Continued)

*Primary Examiner* — Abdullahi Nur
(74) *Attorney, Agent, or Firm* — Robert P. Michal, Esq.; Carter, DeLuca, Farrell & Schmidt LLP

(57) ABSTRACT

A presentation module is provided for presenting a fluid sample to a Laser-induced breakdown spectroscopy (LIBS) analysis. The presentation module comprises an inlet for admitting a fluid sample flow from a process flow, a measurement opening for co-operating with measurement optics, and a stabilizer surface facing towards the measurement opening. The stabilizer surface is adapted to form a stabilized sample flow along the stabilizer surface such that the depth and the outer surface of the sample flow are stabilized, and the surface fluctuation and depth variation of the stabilized sample slurry flow are reduced. As laser pulses are focused on the outer surface of the planar sample flow to transform at least a part of the sample into a state of a plasma, the accuracy and repeatability of the LIBS measurement are significantly improved due to the stabilized sample flow.

13 Claims, 3 Drawing Sheets

(51) Int. Cl.
*G01N 1/20* (2006.01)
*G01N 21/85* (2006.01)
(52) U.S. Cl.
CPC ............... *G01N 2021/8557* (2013.01); *G01N 2201/06113* (2013.01)

(56) References Cited

U.S. PATENT DOCUMENTS

2012/0107851 A1* 5/2012 Killard .............. B01L 3/502753
                                                            435/13
2013/0213115 A1  8/2013 Chu et al.

OTHER PUBLICATIONS

Louis Barrette, et al., "On-Line Iron-Ore Slurry Monitoring for Real-Time Process Control of Pellet Making Processes Using Laser-Induced Breakdown Spectroscopy: Graphitic Vs. Total Carbon Detection" Spectrochimica Acta Part B: Atomic Spectroscopy; vol. 56, No. 6, Jun. 29, 2001, pp. 715-723.
International Search Report for PCT/FI2013/051124 dated Feb. 17, 2014 (3 pages).
Written Opinion of the International Searching Authority issued by the European Patent Office in relation to International Application No. PCT/FI2013/051124 dated Feb. 17, 2014 (7 pages).

* cited by examiner

METHOD AND APPARATUS FOR ONLINE ANALYSIS BY LASER-INDUCED SPECTROSCOPY

CROSS-REFERENCE TO RELATED APPLICATIONS

This application is a National Phase Entry under 35 USC §371 of PCT Patent Application Serial No. PCT/FI2013/051124 filed Dec. 2, 2013, the disclosure of which is expressly incorporated herein by reference in its entirety.

FIELD OF THE INVENTION

The present invention relates to online analysis of a fluid material flow, such as a slurry flow, by laser-induced breakdown spectroscopy.

BACKGROUND OF THE INVENTION

In industrial processes that treat and process slurries containing solid matter, there is often a need to regularly and continuously control the process on the basis of the element contents of the solid matter in the slurry. It is well-known to use certain analysis methods in analyzing slurries that contain solid matter. These include optical methods, nuclear magnetic resonance, and prompt gamma spectroscopy as well as methods utilizing X-rays, such as the method based on X-ray fluorescence. In order to optimally observe and control the industrial processes on the basis of such measurement results, samples are taken continuously from the process flow and analyzed with a delay, which is significantly smaller than the time constant of the process. Mineral separation and hydrometallurgical processes are examples of industrial processes, wherein a real-time analyzing of slurries and liquids are required. Flotation, magnetic and gravity separation, extraction of metals, cleaning of liquid, as well as electrolytic cleaning and recovery processes represent mineral and hydrometallurgy processes that use on-line analyzers.

Laser-induced breakdown spectroscopy (LIBS) is an optical method for performing elemental concentration measurements. LIBS includes generating laser pulses that may be focused toward a sample, such as onto a surface of a sample (e.g., solid or liquid) or into a sample (e.g., liquid or gas). The laser pulse exhibits a high enough power density to transform at least a part of the sample into a state of a plasma. Emitted light from the plasma plume is collected using light collection optics, and the spectral distribution (i.e., intensity as a function of wavelength) of the collected light is analyzed with a spectrometer by generating electronic information describing the spectral distribution of the collected light. Because atomic and molecular constituents of sample materials exhibit a characteristic optical emission spectrum, the information generated by the spectrometer forms a "fingerprint" of the sample material, revealing the constituents of that part of the sample onto which the laser beam was focused. LIBS can provide an easy, fast, and in situ chemical analysis with a reasonable precision, detection limits, and cost.

A prior art arrangement for online analysis of the chemical composition of process flow material with LIBS is disclosed in "On-Stream Analysis (OSA) of Industrial Slurries for Process Control and Optimization Using Laser-Induced Breakdown Spectroscopy (LIBS)", Louis Barrette et al, Proceedings of 36$^{th}$ Annual Meeting of the Canadian Mineral Processors, Paper 17, January 2004. In the prior art arrangement the laser is focused on a steady flow of free-falling slurry. The industrial slurry flow is sampled in three steps. In the first stage, a commercial sampler extracts a portion of the process flow. At the secondary sampling stage, the slurry is conditioned for both flow and density and fed to the injector in such a way to get a smooth free-falling flow suitable for laser sampling. This step is often referred to as a sample presentation. The laser pulse constitutes the final sampler: through energy absorption by the target material, it extracts a µg sample as a short-lived plasma that is analysed with spectroscopic techniques. The output flow is collected and returned to the process. A modified prior art arrangement is disclosed in "Shooting Slurries with Laser-Induced Breakdown Spectroscopy: Sampling is the Name of the Game", Daniel Michaud et al, Applied Optics, Vol. 42, Issue 30, pp. 6179-6183 (2003). The modified sampler geometry, which is shown in FIG. 1, consists of a reservoir 2 with a mechanical stirrer 3, a double-head peristaltic pump 4, a laboratory faucet 5 shaped like an upside-down J, and a rigid receiver tube 6. One end of the receiver tube 6 slips tightly over the tip of the faucet 5; the other end returns the slurry to the reservoir 2. The laser 7 aims the 8-mm-diameter free-falling slurry column through a hole in the receiver tube 6 at a point situated 5 mm below the tip of the faucet 6. Near the strike point, downward aspiration (vacuum) 8 is provided to evacuate nebulized material that results from the laser impact: Inclusion of the upside-down-J-shaped faucet 5 is important to ensure good flow quality minimizing exit splashing. The new sampler has proved successful in circulating high-density iron ore slurries which tend to sediment as well as low-density graphite slurries which tend to float.

These prior art arrangements require very accurate positioning of the laser beam and are sensitive to the surface fluctuation variation of the free-falling slurry flow. The LIBS analysis results have been found to exhibit a strong dependence on the slurry solids content and particle size, when using the described arrangements. With coarser particles and with smaller solids content the sensitivity of the analysis is significantly reduced. Special measures like vacuum suction air flow have been found to be necessary to keep the optical components clean from sample nebulized by the laser pulse.

BRIEF DESCRIPTION OF THE INVENTION

An object of the present invention is to provide a method and an apparatus allowing simpler and more accurate online sampling and analysis of a fluid material flow by laser-induced spectroscopy. The objects of the invention are achieved by a method, an apparatus and a system according to the independent claims. The preferred embodiments of the invention are disclosed in the dependent claims.

An aspect of the invention is an apparatus for presenting a fluid sample to an analyser, the apparatus comprising
   an inlet for admitting a fluid sample flow,
   a measurement opening for co-operating with measurement optics, and
   a stabilizer surface facing towards the measurement opening, the stabilizer surface being adapted to form from the fluid sample flow a thin, stabilized sample flow along the stabilizer surface.

In an embodiment, the stabilizer surface is planar.
In an embodiment, the stabilizer surface is curved.
In an embodiment, the apparatus further comprises a separation device for separating a portion of the fluid sample flow, wherein the stabilizer surface is a part of the separation device and is adapted to form the thin, stabilized sample flow from the portion separated from the fluid sample flow.

In an embodiment, the apparatus further comprises a conduit having an opening communicating with the inlet, the opening being adapted to form the fluid sample flow by diverting a portion of a fluid flow within the conduit to the inlet.

In an embodiment, the fluid flow is pre-classified to contain a component having mainly coarse particles, and the opening for diverting is disposed such that the portion forming the fluid sample flow is taken from said component.

In an embodiment, the apparatus further comprises said measurement optics co-operating with the measurement opening for directing at least one focused laser pulse to induce a plasma in the fluid sample flow on the stabilizer surface and for collecting light emitted by the induced plasma for spectrum analysis.

In an embodiment, the measurement optics comprises collecting optics for collecting the emitted light approximately in a direction perpendicular to the stabilizer surface.

In an embodiment, the apparatus comprises a flat stabilizer body forming said stabilizer surface and having a through-opening in said stabilizer surface at a location of the induced plasma.

In an embodiment, the apparatus comprises a stabilizer sheet or blade forming said stabilizer surface.

In an embodiment, the stabilizer sheet or blade comprises planar or curved sheet or blade.

In an embodiment, the stabilizer sheet or blade or the flat stabilizer is arranged to protrude into the continuous fluid material flow to cut the portion of the continuous fluid material flow.

Another aspect of the invention is a system for on-line analysis of a fluid material flow, such as a slurry flow, by a laser induced spectroscopy, comprising:

an apparatus according to any one of the apparatus embodiments above;

a laser radiation source arranged to generate a laser pulse to induce a plasma in the thin stabilized sample flow on the stabilizer surface;

spectrometer means for spectroscopic analysis of the light emitted by the induced plasma.

A still further aspect of the invention is a method of presenting a fluid sample to an analyser, the method comprising providing a fluid sample flow, forming from the fluid sample flow a thin, stabilized sample flow along a stabilizer surface that faces towards a measurement opening, and co-operating said measurement opening with measurement optics.

In an embodiment, said co-operating comprises sending, through the measurement opening, at least one focused laser pulse to induce a plasma in the stabilized sample flow on the stabilizer surface; and receiving, through the measurement opening, light emitted by the induced plasma for spectrum analysis.

BRIEF DESCRIPTION OF THE DRAWINGS

In the following the invention will be described in greater detail by means of example embodiments with reference to the accompanying drawings, in which.

DESCRIPTION OF EXEMPLARY EMBODIMENTS

Principles of the invention can be applied in any industrial processes that treat and process fluid materials, such as slurries. In embodiments described herein, a fluid material to be sampled and analysed is referred to as a slurry, but embodiments of the invention are not intended to be restricted to this type of fluid material. Mineral separation processes and processes of the hydrometallurgy field are examples of industrial processes, wherein a real-time analysis of slurries and liquids are required. Flotation, magnetic and gravitational separation, extraction of metals, cleaning of liquid, as well as electrolytic cleaning and recovery processes represent mineral and hydrometallurgy processes that may use real-time analysers.

Figure 1:
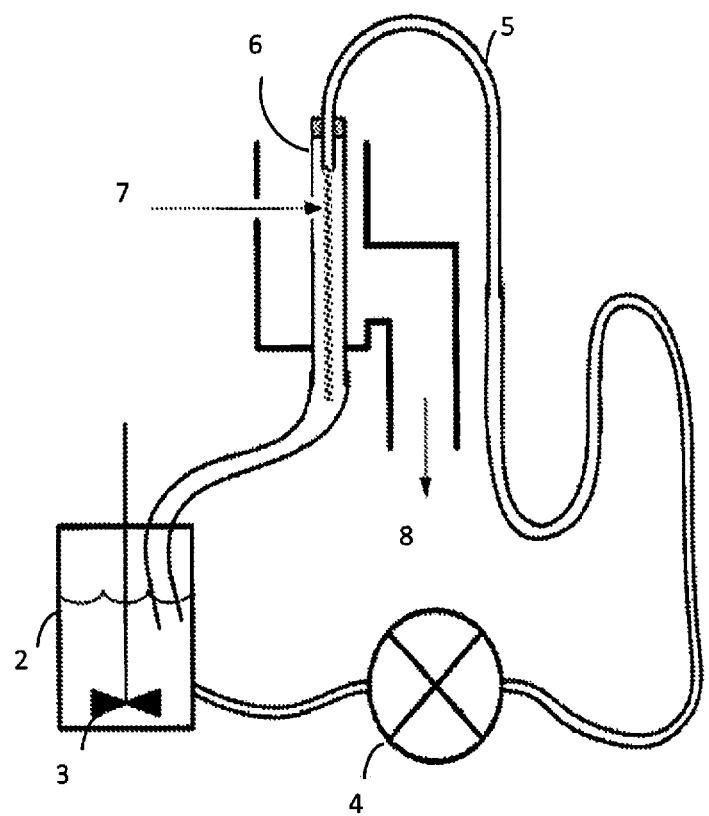
FIG. 1 is a schematic diagram illustrating a prior LIBS art sampling arrangement for process slurry.
Figure 2:
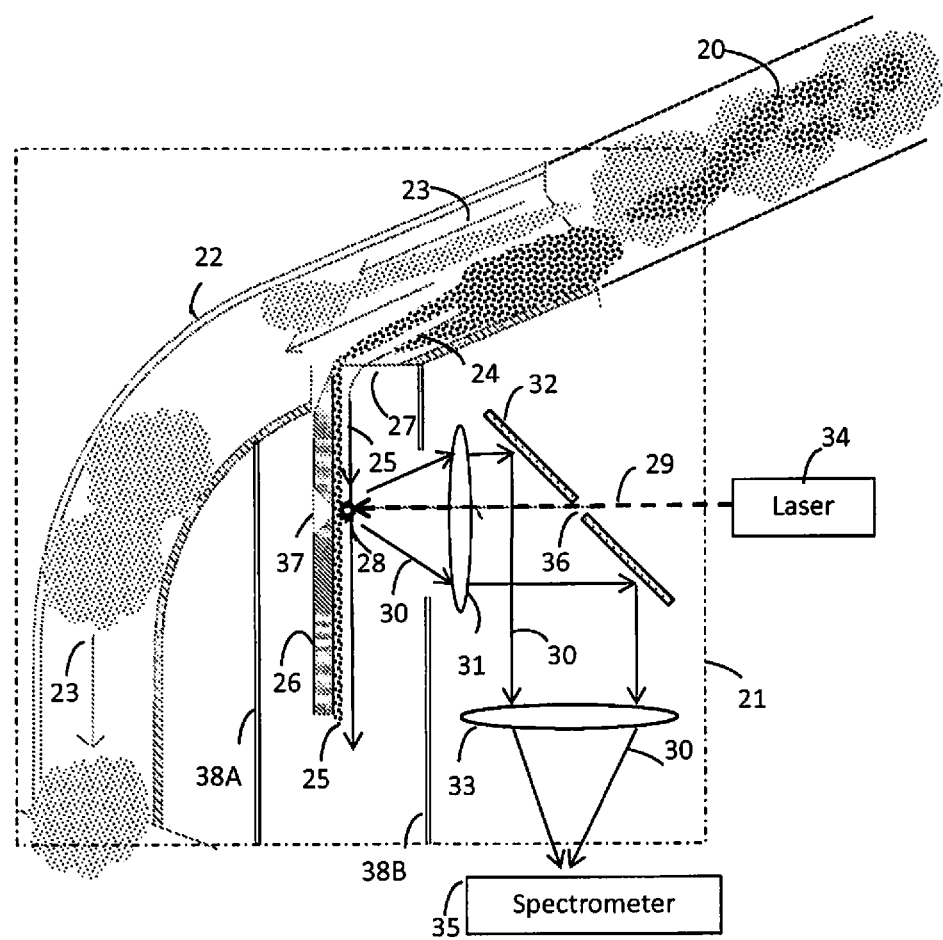
FIG. 2 is a schematic diagram illustrating a LIBS (laser induced breakdown spectroscopy) system according to an exemplary embodiment of the invention.

FIG. 2 is a schematic diagram illustrating a LIBS (laser induced breakdown spectroscopy) system according to an exemplary embodiment of the invention for online sampling and analysis of a fluid material flow, such as a process slurry flow 20. The system may be considered to have two modules: a sample presentation module or sample flow cell 21 and an analysis module.

The sample presentation module 21 may comprise a slurry inlet line or conduit 22 configured to receive the slurry flow 20 from a process piping. The slurry flow 20 may be a primary sample slurry flow (e.g 150 l/min) originating from a primary sampling unit (not shown), such as a sample cutter connected to an actual process slurry line (e.g. 5 to 300 $m^3/h$). Alternatively, the slurry flow 20 may originate from a sample multiplexer to which two or more primary sampling units are connected with dedicated primary sample lines. Thereby, multiple process slurry lines can be analysed with a single analyser.

The main portion 23 of the sample slurry flow 20 may be returned via the slurry inlet line 22 back to the process. A smaller portion 24 of the sample slurry flow 20 may be separated and guided to flow through a bottom opening 27 of the slurry inlet line to form a continuous stabilized sample flow 25 along a stabilizer surface of a stabilizer device or body, such as a stabiliser blade or sheet 26. In the example embodiment shown in FIG. 2, a planar stabilizer blade or sheet 26, is employed, and thereby a planar stabilizer surface is provided. However, alternatively a curved stabilizer blade or sheet, and thereby a curved stabilizer surface may be used. More generally, any structure or body which provides a planar or curved surface suitable to operate as a stabilizer surface may be employed. The selection of a planar surface or the radius of the curvature can be made depending on the type of fluid and/or application. The stabiliser blade may preferably be arranged transversely in relation to the longitudinal axis of the slurry inlet line 22 and the sample slurry flow 20. By the merits of arranging the sample flow 25 to run on the planar or curved surface of the stabilizer blade 25, the depth and the outer surface of the planar sample flow 25 are stabilized, and the surface fluctuation and depth variation of the stabilized sample slurry flow are reduced, or practically avoided. The stabilized sample flow may be relatively thin, e.g. order of few millimeters. As the laser beam is focused and the plasma is induced on the outer surface of the planar sample flow 25, the accuracy and repeatability of the LIBS measurement is significantly improved.

The stabiliser blade 26 may have a form of a planar or curved sheet or plate, for example, and may be fixed transversely to the bottom of the slurry inlet line 25 at the bottom opening 27. The stabiliser blade 26 may arranged in a vertical position and in an inclined position. The stabilizer blade may be made of any material with sufficient corrosion tolerance and durability for the process environment in question. Examples of such materials include metals and ceramics.

In an embodiment of the invention, the top end of the transverse stabiliser blade 26 may be arranged to protrude through the opening 27 inside the slurry inlet line 22 to cut and separate the smaller portion 24 of the sample slurry flow 20 to flow along the stabiliser blade 26. In that case, the stabiliser blade 26 may also be referred to as a cutter blade.

Figure 3:
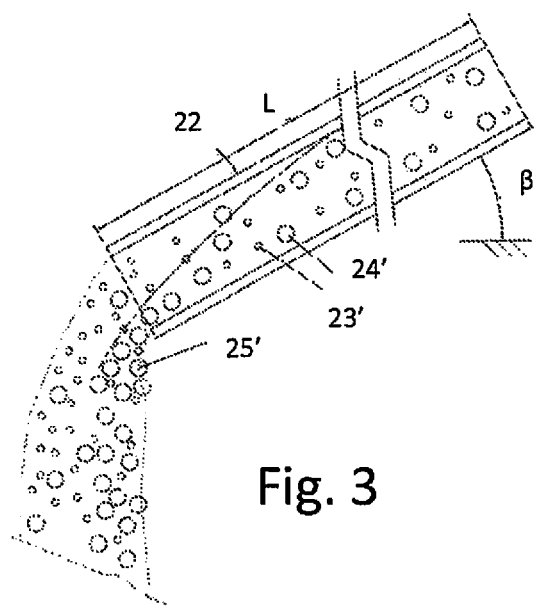
FIG. 3 is a schematic diagram illustrating the classification of slurry particles according to an exemplary embodiment of the invention.

In an embodiment of the invention, zones of different average particle sizes are created in the sample flurry flow 20 prior to the separation or cutting. In the embodiment of FIG. 3, coarse particles may dominate in the first zone which includes the bottom-most portion 24 of the sample slurry flow 20, and finer particles may dominate in top-most portion of the sample slurry flow 20. The bottom-most slurry flow 24 is then separated to as a planar sample flow 25 flow along the stabiliser blade 26. In the LIBS analysis the laser pulse normally vaporize the sample in the measurement point within a depth of micrometers. This makes the LIBS analysis sensitive to the particle size, i.e. the smaller the particle is, the more emission is needed for the measurement. By merits of the classification of the sample slurry 20 such that the relative amount of coarse particles is emphasized in the planar sample slurry flow 25, the sensitivity of the LIBS analysis to the particle size is compensated and the accuracy of the measurement is improved in embodiments of the invention.

The classification before the sample presentation may be implemented by running the sample slurry flow 20 along an inclined, spiral or curvature surface, for example. Alternatively, a mixing chamber or any other equipment or method may be used for the classification. In the embodiment of FIG. 2, the sample presentation module 21 may receive already classified slurry flow 20 from any equipment adapted to perform the classification. The dashed lines in FIG. 2 illustrate an implementation wherein the classification is made in an inclined pipe or line. It should be appreciated that the sample presentation module 21 may also receive an unclassified slurry flow, but in that case the benefits of classification are lost.

Figure 4:
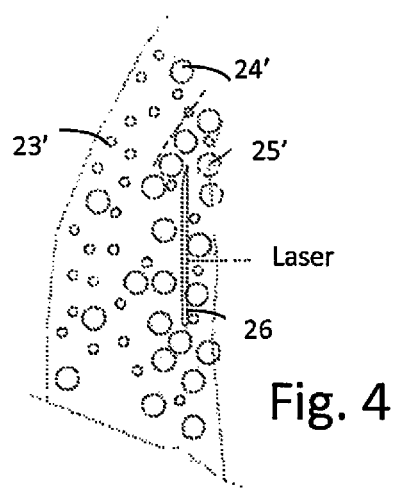
FIG. 4 is a schematic diagram illustrating sampling of classified slurry particles according to an exemplary embodiment of the invention.

FIG. 3 illustrates classification of the slurry particles by an inclined pipe 22' whose longitudinal axis is in an angle β in relation to the horizontal axis. The length of the pipe 22' may be L. When the slurry flow runs downwards in the pipe 22', the larger particles 24' or the sediment tends to move towards the bottom of the pipe 22' while the smaller particles and/or the liquid tend to stay higher in the pipe 22. By an appropriate selection the angle β and the length L, the larger particles 24' or the sediment will dominate in the bottom at the end of the pipe 22' (at the sampling point). The angle β and the length L is to be selected such that the desired level of classification occurs while the pipe 22' will not be blocked by the sedimentation. The higher is the angle β, the shorter can be the length L of the pipe 22'. However, the angle β should be less than 90 degrees. FIG. 4 illustrates the creation of the sample flow of sediment particles 25' along the stabilizer blade 26.

In an embodiment illustrated in FIG. 2, the slurry inlet line 22 continues after the stabilizer blade 26 at the opening 24 in the bottom of the line 22 and bypasses the excess sample slurry 23 in a controlled manner from the sample presentation module back to the process. Splashing of the slurry within the sample presentation module 21 and the size of the sample presentation module 21 can be decreased. However, the principle of providing a sample flow to be analysed to run along a stabilizer blade 26, can be implemented without extension of the inlet line (as illustrated in FIGS. 3 and 4, or with any other type of connection of the stabilizer blade to an inlet line.

In an embodiment of the invention, an opening 37 extending from the first surface to the opposite surface of stabilizer blade 26 is arranged in the stabilizer blade 26 at the focusing point of the laser, as illustrated in FIG. 2. When the laser pulses hit onto a surface of the sample flow 25, it generates a plasma plume 26 having very high initial temperatures that then settle into thermodynamic equilibrium. As it settles into thermodynamic equilibrium, generally within microseconds, the plasma expands and cools. The rapid expansion causes nebulized small droplets of sample to splash towards the optical devices. The droplets tend to slowly contaminate any optical elements along the path from the laser 34 to the sample flow 25, and from the sample flow 25 to the spectrometer 35. The opening 37 in the stabilizer blade 26 allows the energy of the plasma plume 28 to discharge to the opposite side of the stabilizer blade 26, and thereby the splashing of plasma or slurry towards optical devices, such as lenses 20 can be reduced or avoided. The diameter of the opening may be arranged to enlarge in direction from the first surface to an opposite surface of the stabilizer blade 26, e.g. conically. As a further advantage, measuring the sample flow at the opening 37 assures that the measurement occurs from a plasma 28 created in the sample flow 25 and not in the surface of the stabilizer blade 26. In the absence of the sample flow 25, the laser goes through the opening 37 without causing any plasma in the stabilizer blade 26.

In an embodiment illustrated in FIG. 2, the basic presentation module 21 may comprise merely the planar device, such as the stabilizer blade 26, on the surface of which the sample flow is arranged to flow from the inlet. The planar device may be arranged in a sample flow cell confined by housing, such as walls 38A and 38B illustrated in FIG. 2. The sample flow cell may have a measurement opening, such as an opening or window illustrated in the wall 38B, for co-operating with external measurement optics. In other words, the measurement opening allows optical paths to and from the sample flow cell.

The sample presentation module 21 may further comprise optics for focusing the laser beam to the measuring point and for collecting the light emitted by the induced plasma 28. In the embodiment illustrated in FIG. 2, the optics may comprise a lens 31, a mirror 32, and a lens 33. The mirror has an opening through which the laser pulse or pulses 29 from the laser 34 can propagate to the lens 30. The lens 31 may be arranged to focus the laser pulse or pulses 29 to the measuring point. Light 30 emitted from the plasma plume 28 are collected with the lens 31 to the mirror 32 which reflects the emitted light 30 to a collecting lens 33, and the spectral distribution (i.e., intensity as a function of wavelength) is measured. The emitted light 30 collected by the lens may be analyzed with a spectrometer by generating electronic information describing the spectral distribution of the collected emitted light. Because atomic and molecular constituents of sample materials exhibit a characteristic optical emission spectrum, the information generated by the spectrometer forms a "fingerprint" of the sample material, revealing the constituents of that part of the sample onto which the laser beam was focused.

It is advantageous that the laser beam 29 is approximately perpendicular to the surface of the sample flow 25. In case of a curved stabilizer surface the perpendicular laser beam may be aligned with the radius of curvature. In some arrangements it may advantageous to avoid the laser beam being exactly perpendicular to the surface of the sample in order to thereby avoid direct mirror reflection of the laser beam. It should be appreciated that in embodiments of the invention the laser beam may alternatively impact the surface of the sample flow 25 in any angle. Depending on the angle and the measurement arrangement the laser beam 29 may not have to propagate through the mirror 32 and the lens 31 at all.

Even more advantageous is that the emitted light 30 from the plasma plume 28 are collected in a direction perpendicular to the surface of the sample flow 25 such that all of the light emissions are collected. In other words the collecting optics, such as the lens 30, is advantageously arranged such that the collecting optics will cover the largest spatial angle over the plasma plume, thereby providing the highest light intensity and the best analysis sensitivity. The collecting optics may alternatively be arranged in a different position with a smaller spatial angle in relation to the plasma plume, but in that case only part of the light emissions (e.g only from one side) of the plasma plume 28 may collected and the light intensity and the analysis sensitivity is decreased.

It should be appreciated that embodiments of the invention are not intended to be restricted to the illustrated example embodiments of the optics but any suitable optical arrangement may used in association with the invention. A further example of optical arrangements includes focusing a laser beam to a sample surface in a narrow angle (e.g. 45 degrees) by means of first optics and collecting an emitted light in a different direction by means of second optics. The implementation of the optics is not essential to the basic invention.

In the example embodiment shown in FIG. 2, the laser 34 and the spectrometer 35 are illustrated as being separate to the analysis module 21. One or more of the laser 34 and the spectrometer 35 may be directly attached to the sample presentation module, e.g. through a window, or the analysis module 21 and one or more of the laser 34 and the spectrometer 35 may be interconnected by means of optical waveguides, such as optical fibres. It should be appreciated that the laser and the spectrometer or their implementation are not relevant to the invention.

It should also be appreciated that an implemented sample presentation module may contain many further structures and elements not relevant to the basic invention and therefore not discussed or shown herein. For example, there may be various wall and support structures to form a sample chamber wherein the stabilizer blade is located, a housing for optics, adapters for a laser unit, a spectrometer, and/or waveguides, sample windows between different portions of the sample presentation module, sample windows between the sample presentation module, a laser unit and/or a spectrometer, etc.

Upon reading the present application, it will be obvious to a person skilled in the art that the inventive concept can be implemented in various ways. The invention and its embodiments are not limited to the examples described above but may vary within the scope of the claims.

The invention claimed is:

1. An apparatus for presenting a slurry sample to an analyser, the apparatus comprising:
an inlet for admitting a slurry sample flow,
an optical measurement opening for co-operating with external measurement optics, and
a stabilizer surface facing towards the measurement opening, the stabilizer surface being adapted to form from the slurry sample flow a thinner, stabilized sample flow along the stabilizer surface and adapted to present the stabilized sample flow for an optical measurement through said optical measurement opening with the external measurement optics, wherein, for performing the optical measurement, the external measurement optics are adapted to send, through the measurement opening, at least one focused laser pulse to induce a plasma in the stabilized sample flow on the stabilizer surface, and wherein the external measurement optics are adapted to receive, through the measurement opening, light emitted by the induced plasma for spectrum analysis.

2. An apparatus according to claim 1, wherein the stabilizer surface is planar.

3. An apparatus according to claim 1, wherein the stabilizer surface is curved.

4. An apparatus according to claim 1, further comprising a separation device for separating a portion of the slurry sample flow, wherein the stabilizer surface is a part of the separation device and is adapted to form the thin, stabilized sample flow from the portion separated from the slurry sample flow.

5. An apparatus according to claim 1, further comprising a conduit having an opening communicating with the inlet, the opening being adapted to form the slurry sample flow by diverting a portion of a slurry flow within the conduit to the inlet.

6. An apparatus according to claim 5, wherein the opening for diverting is disposed such that the portion forming the slurry sample flow is taken from a component of the slurry flow pre-classified to contain mailing course particles.

7. An apparatus according to claim 1, wherein the measurement optics comprises collecting optics for collecting the emitted light approximately in a direction perpendicular to the stabilizer surface.

8. An apparatus according to claim 1, further comprising a flat stabilizer body forming said stabilizer surface and having a through-opening in said stabilizer surface at a location of the induced plasma.

9. An apparatus according to claim 1, further comprising a stabilizer sheet or blade forming said stabilizer surface.

10. An apparatus according to claim 9, wherein the stabilizer sheet or blade comprises planar or curved sheet or blade.

11. An apparatus according to claim 9, wherein the stabilizer sheet or blade or the flat stabilizer is arranged to protrude into the continuous slurry material flow to cut the portion of the continuous slurry material flow.

12. System for on-line analysis of a slurry material flow, such as a slurry flow, by a laser induced spectroscopy, comprising:
an apparatus according to claim 1;
a laser radiation source arranged to generate a laser pulse to induce a plasma in the thin stabilized sample flow on the stabilizer surface; and
spectrometer means for spectroscopic analysis of the light emitted by the induced plasma.

13. A method of presenting a slurry sample to an analyser, the method comprising:
    providing a slurry sample flow,
    forming from the slurry sample flow a thinner, stabilized sample flow along a stabilizer surface that faces towards a measurement opening and presents the stabilized sample flow for an optical measurement
    through said optical measurement opening with external measurement optics, wherein said optical measurements comprising:
    sending, through the measurement opening, at least one focused laser pulse to induce a plasma in the stabilized sample flow on the stabilizer surface; and
    receiving, through the measurement opening, light emitted by the induced plasma for spectrum analysis.

* * * * *